(12) United States Patent
Smith et al.

(10) Patent No.: US 10,610,258 B2
(45) Date of Patent: *Apr. 7, 2020

(54) OPTICAL OBTURATOR

(71) Applicant: Covidien LP, Mansfield, MA (US)

(72) Inventors: Robert C. Smith, Chapin, SC (US); Thomas Wenchell, Durham, CT (US)

(73) Assignee: Covidien LP, Mansfield, MA (US)

( * ) Notice: Subject to any disclaimer, the term of this patent is extended or adjusted under 35 U.S.C. 154(b) by 274 days.

This patent is subject to a terminal disclaimer.

(21) Appl. No.: 15/689,464

(22) Filed: Aug. 29, 2017

(65) Prior Publication Data

US 2017/0360472 A1 Dec. 21, 2017

Related U.S. Application Data

(60) Continuation of application No. 12/276,632, filed on Nov. 24, 2008, now abandoned, which is a division of
(Continued)

(51) Int. Cl.
*A61B 17/34* (2006.01)
*A61B 17/00* (2006.01)
*A61B 90/00* (2016.01)

(52) U.S. Cl.
CPC .......... *A61B 17/34* (2013.01); *A61B 17/3421* (2013.01); *A61B 90/361* (2016.02);
(Continued)

(58) Field of Classification Search
CPC ............ A61B 17/3417; A61B 17/3421; A61B 17/3423; A61B 2017/3445; A61B 2017/3454
See application file for complete search history.

(56) References Cited

U.S. PATENT DOCUMENTS 3,760,810 A 9/1973 Van Hoorn
4,878,485 A 11/1989 Adair
(Continued)

FOREIGN PATENT DOCUMENTS

EP 0684016 A2 11/1995
EP 0724865 A1 8/1996
(Continued)

OTHER PUBLICATIONS

European Search Report for EP 06005179, date of completion is Sep. 26, 2006 (3 pgs).
(Continued)

*Primary Examiner* — Todd J Scherbel
(74) *Attorney, Agent, or Firm* — Carter, DeLuca & Farrell, LLP

(57) ABSTRACT

An optical obturator apparatus includes an obturator sleeve defining a longitudinal axis and having a longitudinal bore for receiving surgical instrumentation and a transparent window mounted to the obturator sleeve and being dimensioned and configured to pass through tissue. The transparent window is mounted for movement between a first position in general alignment with the longitudinal axis of the obturator sleeve and a second position radially displaced from the longitudinal axis to thereby expose the longitudinal bore of the obturator sleeve to permit passage of the surgical instrumentation. The transparent window may include a cutting blade, or alternatively two cutting blades, adapted to penetrate tissue.

16 Claims, 6 Drawing Sheets

Related U.S. Application Data application No. 11/095,413, filed on Mar. 31, 2005, now Pat. No. 7,470,230.

(52) U.S. Cl.
CPC ............... *A61B 2017/00473* (2013.01); *A61B 2017/347* (2013.01); *A61B 2017/3454* (2013.01)

(56) References Cited

U.S. PATENT DOCUMENTS

| | | | |
|---|---|---|---|
| 5,090,414 A * | 2/1992 | Takano | A61B 8/12 600/446 |
| 5,169,397 A | 12/1992 | Sakashita et al. | |
| 5,176,127 A | 1/1993 | Dormia | |
| 5,226,890 A | 7/1993 | Ianniruberto et al. | |
| 5,250,068 A | 10/1993 | Ideguchi et al. | |
| 5,256,149 A | 10/1993 | Banik et al. | |
| 5,271,380 A | 12/1993 | Riek et al. | |
| 5,290,276 A | 3/1994 | Sewell, Jr. | |
| 5,334,150 A | 8/1994 | Kaali | |
| 5,354,302 A | 10/1994 | Ko | |
| 5,370,640 A | 12/1994 | Kolff | |
| 5,376,076 A | 12/1994 | Kaali | |
| 5,380,291 A | 1/1995 | Kaali | |
| 5,385,572 A | 1/1995 | Nobles et al. | |
| 5,408,992 A | 4/1995 | Hamlin et al. | |
| 5,431,151 A | 7/1995 | Riek et al. | |
| 5,441,041 A | 8/1995 | Sauer et al. | |
| 5,445,142 A | 8/1995 | Hassler, Jr. | |
| 5,467,762 A | 11/1995 | Sauer et al. | |
| 5,551,947 A | 9/1996 | Kaali | |
| 5,562,696 A | 10/1996 | Nobles et al. | |
| 5,569,160 A | 10/1996 | Sauer et al. | |
| 5,569,291 A | 10/1996 | Privitera et al. | |
| 5,569,292 A | 10/1996 | Scwemberger et al. | |
| 5,571,133 A | 11/1996 | Yoon | |
| 5,591,191 A | 1/1997 | Kieturakis | |
| 5,591,192 A | 1/1997 | Privitera et al. | |
| 5,609,562 A | 3/1997 | Kaali | |
| 5,632,717 A | 5/1997 | Yoon | |
| 5,658,236 A | 8/1997 | Sauer et al. | |
| 5,658,306 A | 8/1997 | Kieturakis et al. | |
| 5,662,613 A | 9/1997 | Astarita | |
| 5,662,673 A | 9/1997 | Kieturakis | |
| 5,674,184 A | 10/1997 | Hassler, Jr. | |
| 5,681,323 A | 10/1997 | Arick | |
| 5,685,820 A | 11/1997 | Riek et al. | |
| 5,707,382 A | 1/1998 | Sierocuk et al. | |
| 5,718,664 A | 2/1998 | Peck et al. | |
| 5,720,761 A | 2/1998 | Kaali | |
| 5,738,628 A | 4/1998 | Sierocuk et al. | |
| 5,797,944 A | 8/1998 | Nobles et al. | |
| 5,817,061 A | 10/1998 | Goodwin et al. | |
| 5,843,115 A | 12/1998 | Morejon | |
| 5,857,999 A | 1/1999 | Quick et al. | |
| 5,860,996 A | 1/1999 | Urban et al. | |
| 5,873,889 A | 2/1999 | Chin | |
| 5,980,549 A | 11/1999 | Chin | |
| RE36,434 E | 12/1999 | Hamlin et al. | |
| 6,007,481 A | 12/1999 | Riek et al. | |
| 6,176,824 B1 | 1/2001 | Davis | |
| 6,203,557 B1 | 3/2001 | Chin | |
| 6,206,823 B1 | 3/2001 | Kolata et al. | |
| 6,228,059 B1 | 5/2001 | Astarita | |
| 6,319,266 B1 | 11/2001 | Stellon et al. | |
| 6,350,233 B1 | 2/2002 | Lubowski | |
| 6,402,770 B1 | 6/2002 | Jessen | |
| 6,478,806 B2 | 11/2002 | McFarlane | |
| 6,685,630 B2 | 2/2004 | Sauer et al. | |
| 6,692,467 B2 | 2/2004 | McFarlane | |
| 6,695,816 B2 | 2/2004 | Cassidy, Jr. | |
| 7,056,329 B2 | 6/2006 | Kerr | |
| 7,244,228 B2 | 7/2007 | Lubowski | |
| 7,470,230 B2 * | 12/2008 | Smith | A61B 17/34 600/184 |
| 7,645,289 B2 * | 1/2010 | Bayer | A61B 17/00008 606/159 |
| 2001/0029388 A1 | 10/2001 | Kieturakis et al. | |
| 2002/0099267 A1 * | 7/2002 | Wendlandt | A61B 1/00179 600/173 |
| 2002/0099289 A1 | 7/2002 | Crowley | |
| 2002/0115918 A1 | 8/2002 | Crowley | |
| 2002/0133188 A1 | 9/2002 | O'Heeron et al. | |
| 2002/0143236 A1 | 10/2002 | Sauer et al. | |
| 2002/0169362 A1 | 11/2002 | Kan et al. | |
| 2002/0188201 A1 | 12/2002 | Crowley | |
| 2003/0187471 A1 | 10/2003 | Cooper | |
| 2004/0015182 A1 | 1/2004 | Kieturakis et al. | |
| 2004/0066008 A1 | 4/2004 | Smith | |
| 2004/0082969 A1 | 4/2004 | Kerr | |
| 2005/0033304 A1 | 2/2005 | O'Heeron | |
| 2005/0107816 A1 | 5/2005 | Pingleton et al. | |
| 2005/0192613 A1 | 9/2005 | Lindsay | |

FOREIGN PATENT DOCUMENTS

| | | |
|---|---|---|
| EP | 0815796 A2 | 1/1998 |
| EP | 1036544 A1 | 9/2000 |
| EP | 1685792 A1 | 8/2006 |
| EP | 1994897 A2 | 11/2008 |
| JP | 05-068666 | 3/1993 |
| JP | 2004-261344 A | 9/2004 |
| WO | 95/13751 A1 | 5/1995 |
| WO | 03/075999 A1 | 9/2003 |
| WO | 2004002337 A1 | 1/2004 |
| WO | 2008/045316 A2 | 4/2008 |

OTHER PUBLICATIONS

European Search Report from EP Application No. EP 11 00 4282 dated Feb. 10, 2014, 5 pages.
European Search Report EP 08 25 3194 dated Feb. 17, 2009.
Japanese Office Action (Japanese Patent Appln. No. 2006-047568) dated Sep. 5, 2011.
Dictionary.com, http://dictionary.reference.com/browse/secure as accessed on Jul. 31, 2015.

* cited by examiner

OPTICAL OBTURATOR

CROSS REFERENCE TO RELATED APPLICATION

The present application is a continuation of U.S. patent application Ser. No. 12/276,632, filed Nov. 24, 2008, which is a divisional application which claims the benefit of and priority to U.S. patent application Ser. No. 11/095,413 filed Mar. 31, 2005, (now U.S. Pat. No. 7,470,230) the entire contents of which are incorporated herein by reference.

BACKGROUND

1. Technical Field

The present disclosure relates to an apparatus for penetrating body tissue during minimally invasive surgical procedures, such as endoscopic or laparoscopic procedures. More particularly, the present disclosure relates to an access assembly having a transparent window for providing visual observation during penetration of the peritoneum or other body tissue.

2. Background of the Related Art

Minimally invasive surgical procedures including endoscopic and laparoscopic procedures permit surgery to be performed on organs, tissue and vessels far removed from an opening within the tissue. Laparoscopic and endoscopic procedures are performed in the interior of the abdomen through a small incision such as, for example, a narrow endoscopic tube or cannula inserted through a small entrance incision in the skin. Typically, after the abdominal cavity is insufflated, a trocar is used to puncture the cavity wall, i.e., the peritoneal lining, to create a pathway to the underlying surgical site. Generally, the trocar includes a stylet or obturator having a sharp tip for penetrating the body cavity, which is positioned coaxially within an outer cannula. The obturator is removed, leaving the outer cannula in place for reception of instrumentation utilized to perform the surgical procedure. An example of a known trocar is described in commonly assigned U.S. Pat. No. 6,319,266 to Stellon, which issued Nov. 21, 2001, the contents of which are incorporated herein in its entirety by reference. However, with known trocars, advancement of the obturator through tissue is typically performed blind, i.e., without visualization of the tissue being entered. Obturators allowing visualization include U.S. Pat. Nos. 5,334,150, 5,431,151 and 5,441,041.

Accordingly, the present disclosure provides an optical access assembly which permits direct visualization of body tissue during penetration of the body cavity. Moreover, the optical access assembly of the present disclosure provides an improved structure for direct visualization of the body tissue being penetrated and serves as a conduit for subsequent introduction of surgical instrumentation required for performance of the surgical procedure.

SUMMARY

In one preferred embodiment, an optical obturator apparatus includes an obturator sleeve defining a longitudinal axis and having a longitudinal bore for receiving surgical instrumentation and a transparent window mounted to the obturator sleeve and being dimensioned and configured to pass through tissue. The transparent window is mounted for movement between a first position in general alignment with the longitudinal axis of the obturator sleeve and a second position radially displaced from the longitudinal axis to thereby expose the longitudinal bore of the obturator sleeve to permit passage of the surgical instrumentation. The transparent window may include a cutting blade, or alternatively two cutting blades, adapted to penetrate tissue.

A control member is connected to the transparent window and at least partially extends along the obturator sleeve. The control member is actuable to move the transparent window between the first position and the second position. The control member is adapted to rotate about an axis of rotation to cause movement of the transparent window between the first position and the second position. In this regard, the transparent window is adapted for pivotal movement about the axis of rotation to move between the first position and the second position thereof. The control member may be adapted to move in a longitudinal direction from a normal position to an extended position to displace the transparent window relative to the obturator sleeve.

An anti-rotation member may be associated with the transparent window to prevent pivotal movement of the transparent window when the transparent window is in the normal position thereof. The anti-rotational member includes a key extending from one of the transparent window and the obturator sleeve, the key receivable within a keyed port defined in the other of the transparent window and the obturator sleeve. The key is removed from the keyed port upon movement of the control member to the extended position.

A manually manipulative member may be operatively connected to the control member. The manually manipulative member is movable to move the control member.

In another preferred embodiment, a surgical optical viewing system includes an optical obturator having an obturator sleeve defining a longitudinal axis and a longitudinal bore for reception of surgical instrumentation. The optical obturator includes a transparent window for permitting passage of light into the obturator sleeve. The transparent window has at least two separable window sections. The at least two separable window sections are adapted for radial displacing movement to expose the longitudinal bore and to permit passage of the surgical instrumentation used for performing a surgical procedure. The transparent window may define a tapered configuration and at least one cutting blade adapted to penetrate tissue.

The optical viewing system may further include a surgical instrument positionable within the longitudinal bore of the obturator sleeve. The at least two separable sections of the transparent window are adapted for radially displacing movement in response to longitudinal movement of the surgical instrument relative to the obturator sleeve. In this regard, the surgical instrument is engageable with interior surfaces of the at least two separable sections of the transparent window upon relative longitudinal movement of the surgical instrument and the obturator sleeve to radially displace the at least two separable sections.

BRIEF DESCRIPTION OF THE DRAWINGS

Preferred embodiments of the present disclosure are described hereinbelow with references to the drawings, wherein.

DETAIL DESCRIPTION OF PREFERRED EMBODIMENTS

Figures 1, 4:
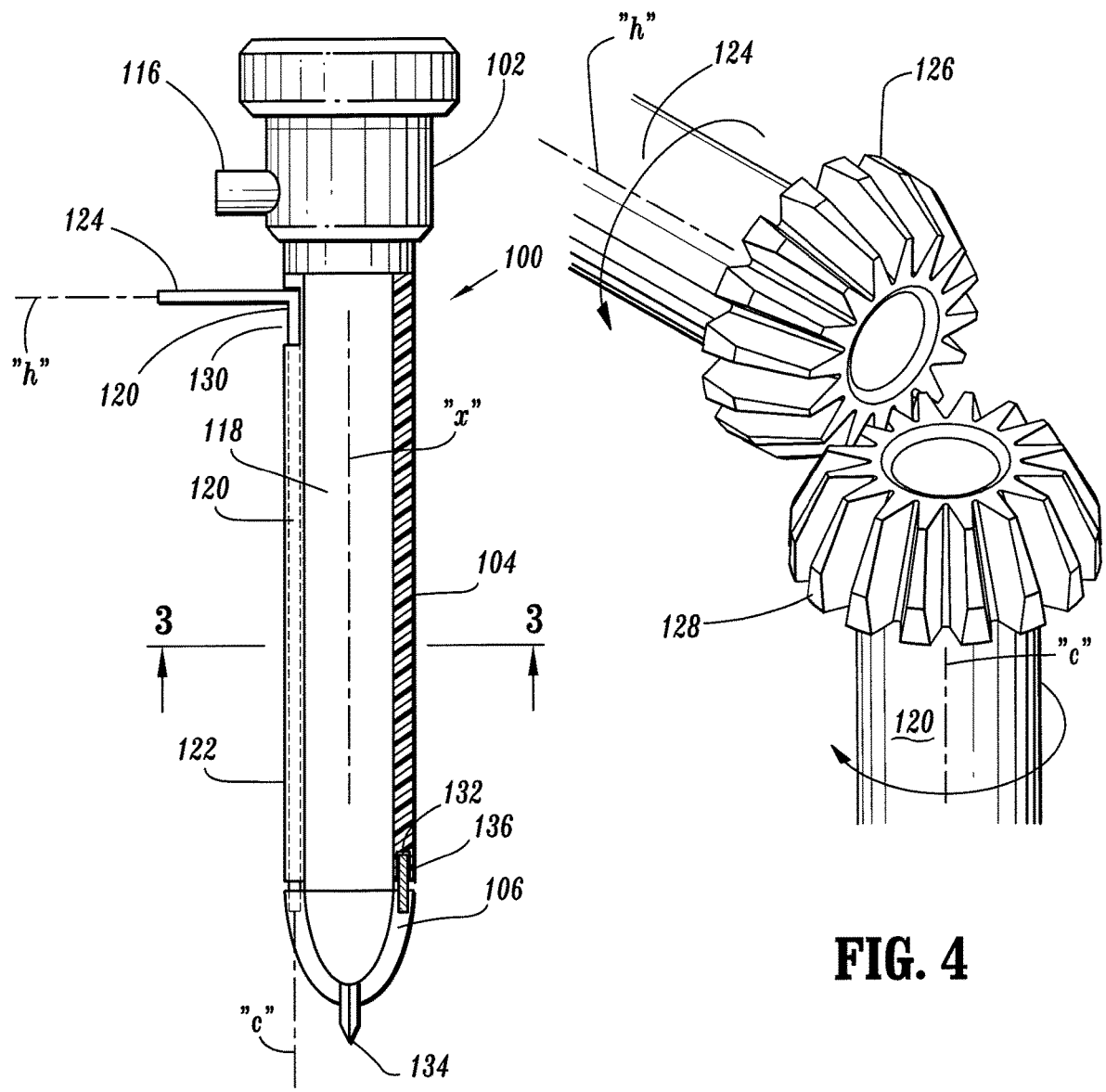
FIG. 1 is a side view in partial cross-section of one embodiment of an optical access assembly constructed in accordance with the present disclosure.
FIG. 4 is a view illustrating a bevel gear arrangement associated with the sleeve of the optical access assembly in accordance with the embodiment of FIGS. 1-3.

Referring now in detail to the drawing figures, in which, like reference numerals identify similar or identical elements, there is illustrated in FIG. 1, an optical access assembly constructed in accordance with a preferred embodiment of the present disclosure, and designated generally by reference numeral 100. Optical access assembly 100 contemplates the direct visualization of body tissue during penetration of the peritoneal cavity or other tissue portions. In addition, optical access assembly 100 facilitates the introduction of various types of surgical instruments such as, for example, an endoscopic clip applier, grasper, dissector, retractor, stapler, photographic device, tube, and the like. Optical access assembly 100 is dimensioned to pass through body tissue and may incorporate structure to cut, puncture, or pierce the body tissue.

Figure 2:
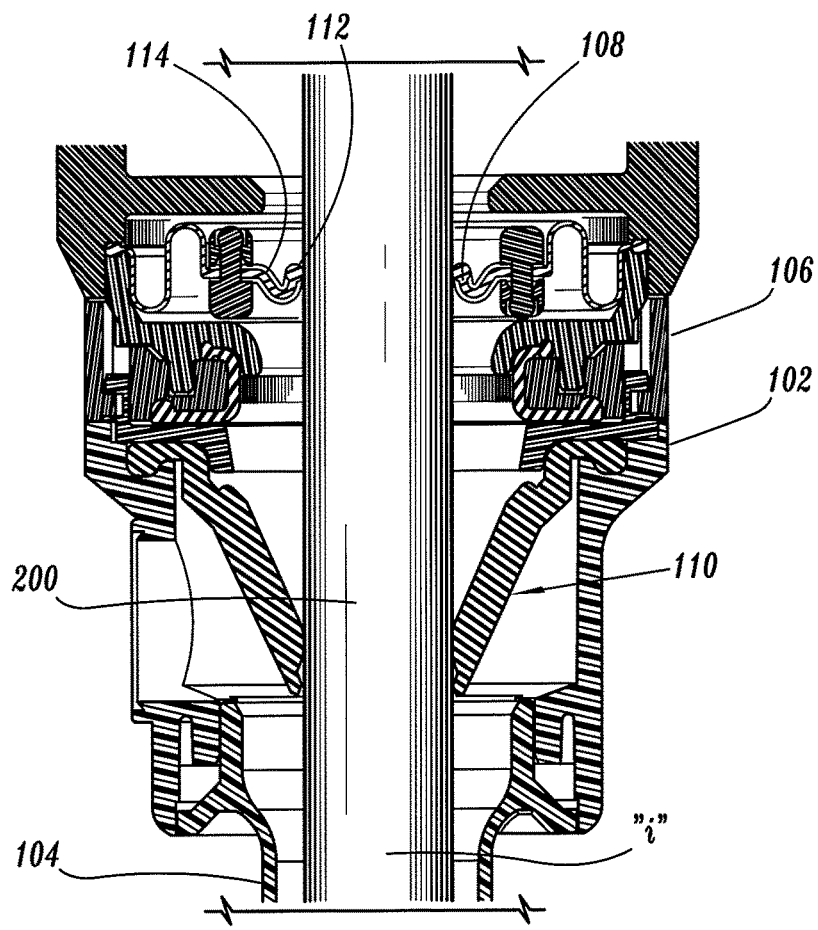
FIG. 2 is an enlarged side cross-sectional view of the housing of the access assembly in accordance with the embodiment of FIG. 1 illustrating the sealing system for forming a fluid tight seal about a surgical instrument.

Generally, optical access assembly 100 includes housing 102, sleeve 104 secured to housing 102 and extending distally therefrom and window 106 operatively connected to the distal end of sleeve 104. Housing 102 may incorporate several components connected to each other by conventional means or may be a single component. As best depicted in FIGS. 1-2, housing 102 is advantageously dimensioned to be grasped by the surgeon. Housing 102 includes an internal sealing system to receive a surgical instrument in substantial sealed relation therewith while also providing a substantial seal between the body cavity and the outside atmosphere both during, and subsequent to, insertion of the surgical instrument through sleeve 104. One exemplative sealing system suitable for use in optical obturator assembly 100 is shown in FIG. 2. This sealing system is disclosed in commonly assigned U.S. Published Application No. 2004/0066008 to Smith, the entire contents of which are hereby incorporated by reference. The sealing system includes instrument seal 108 and zero-closure seal 110. Instrument seal 108 is formed of a resilient material and has an aperture 112 for sealed reception of a surgical instrument. A fabric layer 114 is juxtaposed relative to the resilient material and may be disposed on either, or both of, the proximally facing surface or distally facing surface of instrument seal 108. The preferred fabric includes a SPANDEX™ material containing 20% LYCRA from Milliken. Zero closure valve 110 is preferably a duck bill valve which opens to permit passage of the surgical instrument. Duck bill valve 110 desirably closes in the absence of the surgical instrument and/or in response to the pressure of the insufflation gases. Housing 102 further includes insufflation connector or port 116 (FIG. 1). Insufflation connector 116 is adapted for connection to a supply of insufflation gases for introduction within the peritoneal cavity as is conventional in the art. Further details of the sealing system may be ascertained by reference to the Smith '008 publication.

Figure 3:
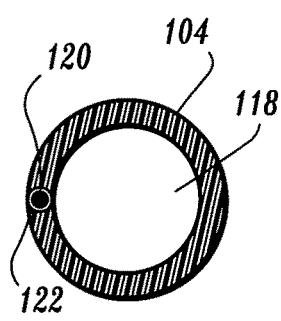
FIG. 3 is a cross-sectional view of the obturator sleeve of the optical access assembly in accordance with the embodiment of FIGS. 1-2 and taken along section lines 3-3 of FIG. 1.

With reference to FIGS. 1 and 3, sleeve 104 defines longitudinal axis "x" and has longitudinal bore 118 extending the length of the sleeve 104. Longitudinal bore 118 permits the introduction of a surgical instrument utilized in the surgical procedure. Sleeve 104 preferably has a diameter of between about 4 millimeters to about 14 millimeters. Sleeve 104 may be constructed of a medical grade metal including stainless steel or titanium or a suitable biocompatible polymeric material. Sleeve 104 further includes control member 120 (shown partially in phantom in FIG. 1) which extends through passage 122 defined in the sleeve 104. Control member 120 serves to mount transparent window 106 and also moves the transparent window 106 between a first position aligned with longitudinal axis and a second position displaced from the longitudinal axis "x". In this regard, control member 120 is adapted to rotate within passage 122 (i.e., about an axis of rotation "c" which is in general parallel to axis "x" of obturator sleeve 104) and is also adapted for limited longitudinal movement within passage 122.

A manual manipulative handle 124 extends radially outwardly from the proximal end of control member 120. Handle 124 is advantageously dimensioned for gripping engagement by the user and is actuable to effectuate rotational and/or longitudinal movement of control member 120 and thus corresponding movement of window 106. More specifically, handle 124 is mechanically connected to control member 120 in a manner whereby rotational movement of the handle 124 about handle axis "h" causes corresponding rotational movement of the control member 120 about axis "c". Any means for transferring this rotational motion are envisioned including, e.g., the bevel gear arrangement depicted in FIG. 4. In this regard, handle 124 may be integrally formed with first gear 126 and control member 120 may be integrally formed with second gear 128. First and second gears 126, 128 cooperate whereby rotational movement of handle 124 and first gear 126 about handle axis "h" causes corresponding rotational movement of control member 120 about control axis "c". The bevel gear arrangement may be appropriately miniaturized to reside within passage 122 of the wall of obturator sleeve 104 or may be disposed within housing 102. In addition, handle 124 is adapted to move in the longitudinal direction within slot 130 of obturator sleeve 104 in response to proximal and distal applications of force by the surgeon.

Sleeve 104 further defines keyed notch 132 in its distal end. Keyed notch 132 serves to prevent rotation of window 106 during introduction within the body tissue.

Figure 5:
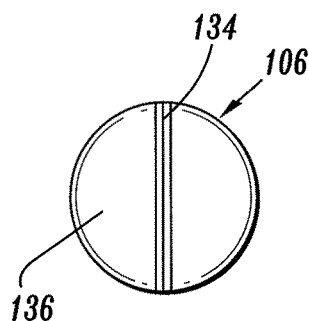
FIG. 5 is a an axial view illustrating the transparent window of the optical access assembly in accordance with the embodiment of FIGS. 1-4.

Referring now to FIGS. 1 and 5, window 106 will be discussed in detail. Window 106 permits visualization during penetration of the body tissue. Window 106 may comprise a transparent or translucent polymeric material and be fabricated via known injection molding techniques. Alternatively, window 106 may comprise an optical glass. The term "transparent" is to be interpreted as having the ability to permit the passage of light with or without clear imaging capabilities. Moreover, the transparent material includes any material which is not opaque. It is also to be appreciated that only a portion of transparent window 106 needs to be transparent. Thus, a portion of, or the entire window 106, may be transparent or translucent. Window 106 may have a unitary construction or be comprised of multiple parts.

Window 106 is generally tapered in configuration, e.g., bulbous, hemispherical, or pyramidal conically-shaped, to facilitate passage through body tissue. Window 106 may include an image directing member (not shown) for directing optical images into longitudinal bore 118 of sleeve 104 or back to an image apparatus. The image directing member may be a lens, an optical prism, an optical mirror, or like image directing medium.

Figure 6:
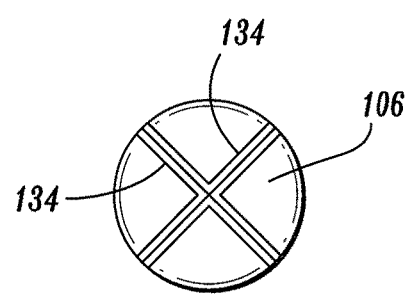
FIG. 6 is view of an alternative embodiment of the transparent window of the optical access assembly.

As best depicted in FIG. 3, transparent window 106 preferably has at least one cutting blade 134. Cutting blade 134 is preferably centered with respect to the outer surface 136 of window 106, as shown. Thus during visualization, cutting blade 134 is seen as a thin line through the center, i.e. bisecting the viewing field so as not to substantially obstruct viewing of the body tissue. Cutting blade 134 may be an independent member secured to outer surface 136 by conventional means including welding, cements, etc. Alternatively, cutting blade 134 may be integrally formed with window 106 during, e.g., in a molding process. In this embodiment, cutting blade 134 is made of a polymeric material and is integrally formed with window 106. form. In one embodiment, cutting blade 134 includes a single cutting blade. Alternatively, two intersecting cutting blades 134 arranged in an X pattern, may be provided as shown in FIG. 6. Other arrangements of cutting blade 134 are envisioned, such as, for example, arrangements of three, four, etc., of the cutting blades 134. One or more cutting blades 134 may be disposed along lateral sides of window 106.

Window 106 further includes anti-rotation key 136. Anti rotation key 136 resides within keyed notch 134 of sleeve 104 to prevent rotation of the sleeve 104 during introduction of window 106.

In operation, the peritoneal cavity is insufflated to raise the cavity wall to provide greater access to tissue and organs therewithin. An endoscope 200 is inserted into optical access assembly 100, i.e., through housing 102 and into longitudinal bore 118, as shown in FIG. 2. One suitable endoscope for use with optical access assembly 100 is disclosed in commonly assigned U.S. Pat. No. 5,718,664 to Peck et al., the contents of which are incorporated herein by reference. Instrument seal 108 of housing 102 forms a fluid tight seal about the endoscope 200. As appreciated, endoscope 200 is advanced within sleeve 104 until the distal end of the endoscope 200 is adjacent window 106. In this position, the distal lens element of the endoscope 200 is capable of viewing the tissue being entered. Endoscope 200 may be secured relative to optical obturator assembly 100 with a locking system (not shown), at the proximal end of the optical access assembly 100, at some location along sleeve 104, or at the distal end of sleeve 104. For example, the locking mechanism may comprise a cam mechanism, or a ledge at the distal end of sleeve 104.

The procedure is continued by positioning window 106 against the body tissue "t" and advancing the assembly 100 to permit cutting blade 134 to penetrate the tissue. A skin incision may be made before pressing window 106 against the tissue, if desired. During penetration of the body tissue, the surgeon observes the underlying tissue through the endoscope 200 to ensure there is no undesired contact with organs, tissue, etc. lying beneath the peritoneal lining. In instances where a video system is utilized, the surgeon simply observes the penetration of body tissue "t" via any known video monitor. Once the surgeon penetrates the body tissue "t" as observed through the endoscope 200, the surgeon discontinues the application of force. For example, in penetration of the abdominal wall, the surgeon can observe the peritoneum and penetration thereof.

Figure 8:
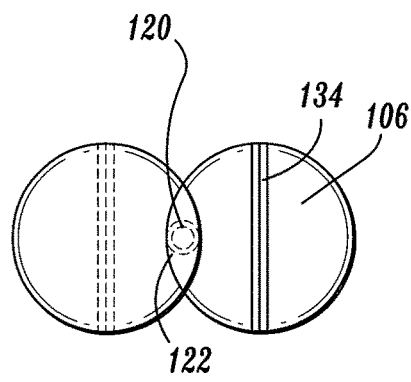
FIG. 8 is an axial view further illustrating movement of the transparent window from the first position to the second position in accordance with the embodiment of FIGS. 1-5 and 7.
Figure 7:
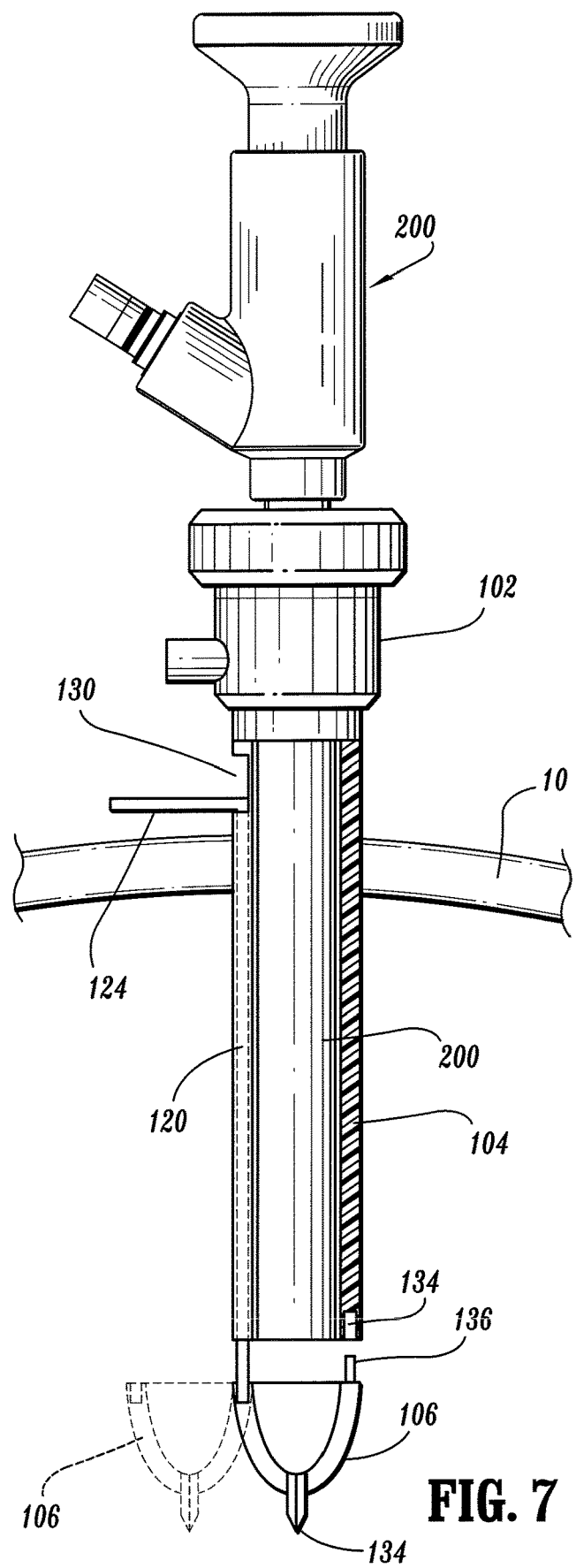
FIG. 7 is a side view in partial cross-section of the optical access assembly in accordance with the embodiment of FIGS. 1-5, illustrating movement of the transparent window from a first positioned aligned with the sleeve and a second position displaced from the sleeve.
Figure 9:
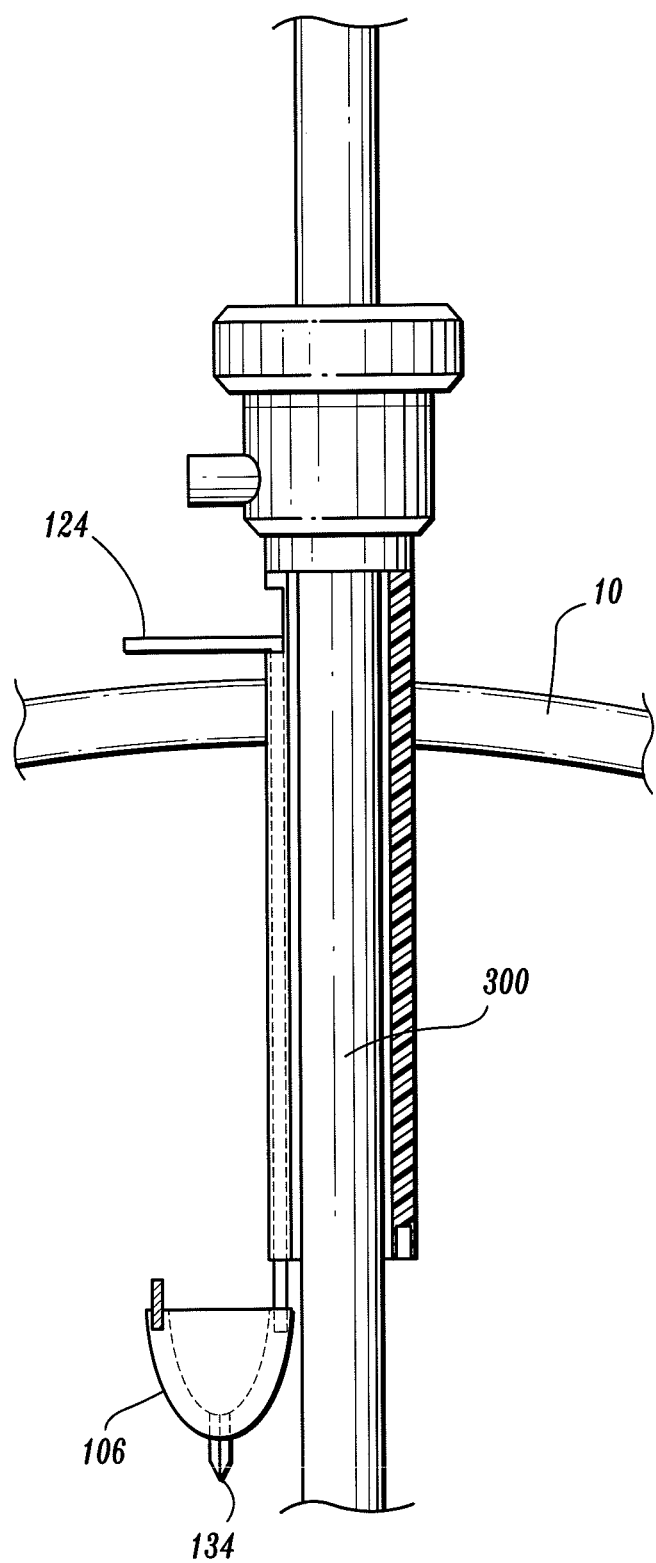
FIG. 9 is a view similar to the view of FIG. 7 illustrating advancement of a surgical instrument through the sleeve and beyond the transparent window for performing a surgical procedure.

After penetration into the underlying body cavity, handle 124 is moved in the distal direction within slot 130 of obturator sleeve 104 to move control member 120 from its normal operative position depicted in FIG. 1 to the extended position depicted in FIG. 7. During this distal movement, anti-rotation key 136 of transparent window 106 clears keyed notch 134 within obturator sleeve 104. Once key 136 is cleared from its containment within keyed notch 134, handle 124 is rotated about handle axis "h" (FIG. 4) which causes corresponding rotation of control member 126. The rotational movement of control member 120 causes transparent window 106 to rotate around axis of rotation "c" to the radially displaced position depicted in FIGS. 7 and 8. In this position, longitudinal bore 118 of sleeve 104 is exposed. Endoscope 200 may then removed from longitudinal bore 120 for insertion of other desired surgical instruments 300 to carry out the desired procedure as shown in FIG. 9. Although FIG. 7 shows an endoscope 200 with an eye piece, the endoscope 200 may be additionally or alternatively connected to an imaging system, which may include a computer.

Figure 10:
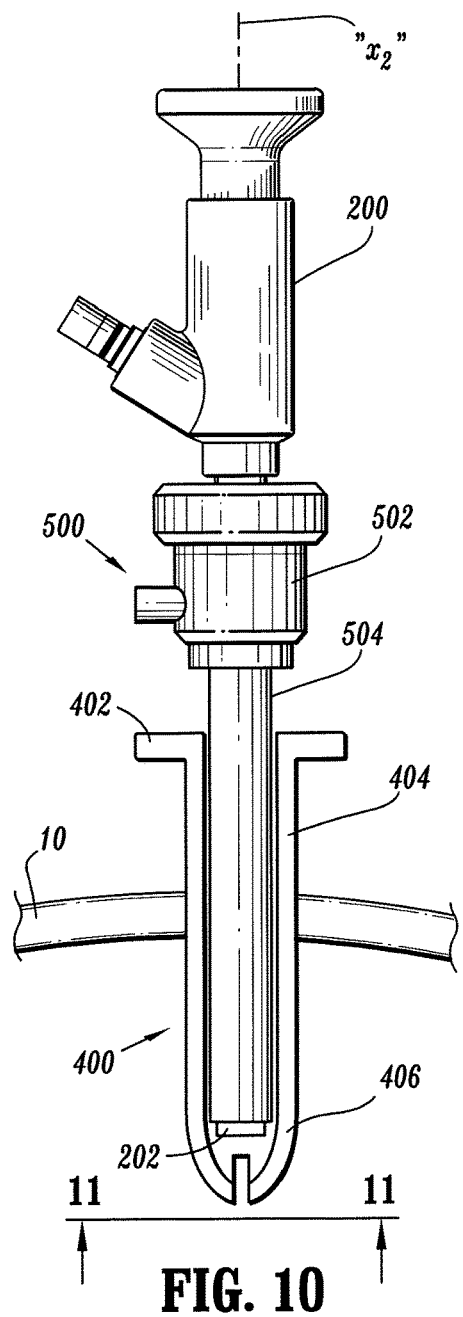
FIG. 10 is a side view in partial cross-section of an alternative embodiment of an optical access assembly of the present disclosure.
Figure 12:
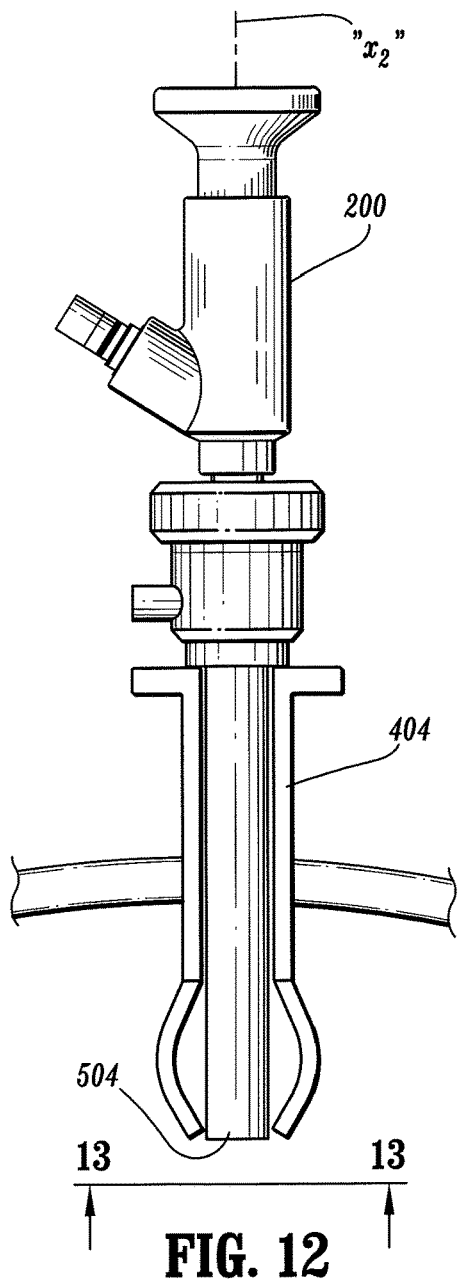
FIG. 12 is a view similar to the view of FIG. 10 illustrating radial movement of the window segments of the transparent window to open the sleeve of the optical access assembly in accordance with the embodiment of FIGS. 10-11.

With reference to FIGS. 10-13, an alternative embodiment of an optical obturator assembly of the present disclosure is illustrated. In FIG. 10, optical access assembly 400 is shown with a cannula assembly 500 at least partially positioned therein and a conventional endoscope 200 introduced within the cannula assembly 500. Optical access assembly 400 generally includes handle 402 and sleeve 404 extending distally from the handle 402. Handle 402 and sleeve 404 may be separate components or integrally formed during manufacture. Adjacent the distal end of sleeve 404 is window 406. Window 406 is transparent or translucent as discussed hereinabove and preferably is integrally formed with sleeve 404. Window 406 includes a plurality of individual separable window sections 408 (FIG. 12) which are capable of radial displacement to permit passage of a surgical instrument. Desirably, window 406 and/or the entire sleeve 404 is made from a relatively flexible material. In the preferred embodiment, four window segments 408 are provided with each of the segments 408 separated from adjacent segment 408 by respective slits 410. Window 406 further includes a pair of intersecting cutting blades 412. Cutting blades 412 function in penetrating or piercing body tissue.

Cannula assembly 500 may be similar to any conventional cannula assembly adapted for use in laparoscopic surgery. Cannula assembly 500 includes cannula housing 502 and cannula 504 extending from the cannula housing 502. An internal seal assembly may be mounted within cannula housing 502 for sealed reception of a surgical instrument such as an endoscope. One suitable seal system is disclosed hereinabove in connection with the discussion of FIG. 2 any suitable seal system for cannula assemblies may be used.

Figure 11:
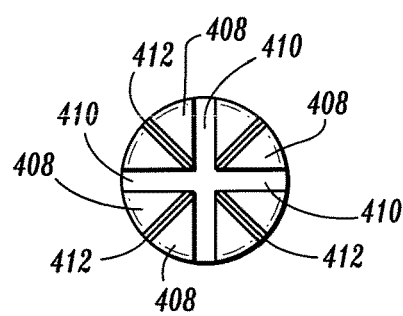
FIG. 11 is an axial view illustrating the transparent window in accordance with the embodiment of FIG. 10.
Figure 13:
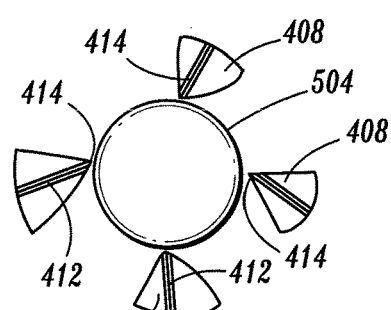
FIG. 13 is axial view further illustrating the radial movement of the window segment of the transparent window.

In operation, cannula assembly 500 is positioned within optical access assembly 400 followed by insertion of an endoscope 200 within the cannula assembly 500. Endoscope 200 is positioned within access assembly 400 such that distal lens element 202 of endoscope 200 does not extend beyond the distal end of access assembly 400 as shown in FIG. 10. Thereafter, the surgeon penetrates the body tissue "t" while observing the penetration through the eyepiece of the endoscope 200 (or while observing the same on an imaging and/or computer screen), as described in detail hereinabove. Endoscope 200 may then be removed if desired. Subsequent to penetration of the body cavity, the surgeon engages handle 402 to move sleeve 404 in the proximal direction as depicted in FIG. 11. Proximal movement of obturator sleeve 404 causes the distal end of cannula 504 to engage internal surfaces 414 of window sections 408. Accordingly, window sections 408 are biased outwardly to the arrangement shown in FIG. 13. In this position, window sections 408 are radially displaced from longitudinal axis "X" to thereby expose cannula 504, thus permitting passage of surgical instrumentation through the cannula 504 and into the underlying body cavity.

Figure 14:
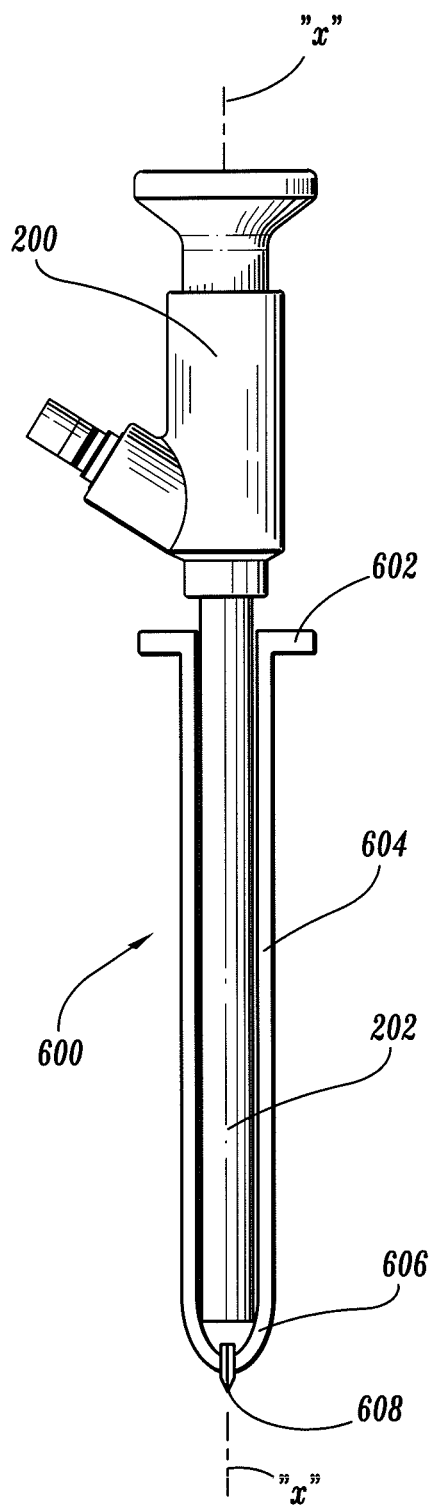
FIG. 14 is a side view in partial cross-section of another embodiment of an optical access assembly of the present disclosure.

With reference to FIG. 14, another embodiment of an optical access assembly of the present disclosure is illustrated and designated generally as optical access assembly 600. Access assembly 600 generally includes handle 602 and sleeve 604 defining a longitudinal axis "X". A window 606 having cutting blade 608 is formed at the distal end of sleeve 604. Desirably, the window 606 is transparent or translucent, as discussed above in connection with FIGS. 1, 5 and 10. Endoscope 200 is positioned within sleeve 604 to provide for observation of the body tissue being penetrated. Endoscope 200 includes an endoscopic shaft 202 which is frictionally engaged by the internal surfaces of sleeve 604, i.e., sleeve 604 may be dimensioned to form a friction fit with the endoscopic shaft 202 to thereby retain endoscope in a desired position relative to sleeve 604 with the distal lens component adjacent window 606. Alternatively, a locking system, as discussed above in connection with FIG. 2, may be used. In use of this embodiment, endoscope 200 in positioned within access assembly 600 and the desired frictional relationship is established between endoscopic shaft 202 and access sleeve 604. The system is advanced through the tissue with visualization provided by endoscope 200 through window 206.

In further embodiments, the optical access assembly is as discussed above in connection with FIGS. 1-5 and 7-9, except that the window has window sections that are arranged as jaws pivotally mounted on the distal end of the sleeve. An elongated member extending proximally, along the sleeve, cooperates with a handle or other structure for actuating the jaws. During actuation, the jaws move from a closed position to an open position. The jaws may or may not include blades. The jaws, when in a closed position, may have any shape, such as pyramidal, conical, dolphin-nosed, hemispherical, etc. The pivotable jaws are translucent or transparent, as discussed above, and the user of the optical access assembly views tissue before, during and after advancement of the optical access assembly. The jaws may be actuated while the assembly is advanced through tissue, or after the tissue has been penetrated and the body cavity accessed.

In further embodiments, the optical access assembly is as discussed above in connection with FIGS. 1-5 and 7-9, except that the window comprises a closed, pyramidal, conical, dolphin-nosed, and/or preferably hemispherical shape. An elongated member extending proximally, along the sleeve, cooperates with a handle or other structure for rotating the window away from the distal end of the sleeve. The window rotates from a position closing the distal end of the sleeve, to a position that leaves the distal end of the sleeve open. The window may or may not include one or more blades. The user of the optical access assembly views tissue before, during and after advancement of the optical access assembly.

In each of the embodiments discussed above, the window may or may not include cutting blades. The window may have any shape, such as pyramidal, conical, dolphin-nosed, hemispherical, etc. In each of the embodiments discussed above, the endoscope may include an eyepiece, and/or a connection to imaging equipment which may include a computer. In each of the embodiments discussed above, the movement of the window, jaws, or window sections is driven by an electric motor, hydraulic driver or manual drive and may be controlled utilizing electrical or mechanical methods.

It will be understood that various modifications can be made to the embodiments of the present invention herein disclosed without departing from the spirit and scope thereof. For example, various diameters for the obturator assembly, cannula assembly, as well as various diameters for the surgical instruments are contemplated. Also, various modifications may be made in the configuration of the parts. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. An optical access apparatus, comprising:
   an obturator sleeve defining a passageway, the passageway defining a longitudinal axis and configured to receive surgical instrumentation at least partially therethrough; and
   a tip disposed adjacent a distal end of the obturator sleeve and configured to separate tissue, the tip being rotatable about an axis of rotation parallel to the longitudinal axis between a first position where a distal end of the tip is in general alignment with the longitudinal axis and a second position where the distal end of the tip is offset from the longitudinal axis,
   wherein the obturator sleeve includes a notch defined within the distal end thereof, and wherein the tip includes a key configured to selectively engage the notch to help prevent rotation of the tip relative to the obturator sleeve.

2. The optical access apparatus according to claim 1, wherein when the tip is in the first position, the tip restricts surgical instrumentation from being advanced through the passageway to a position that is distally beyond the tip.

3. The optical access apparatus according to claim 2, wherein when the tip is in the second position, surgical instrumentation is permitted to advance through the passageway to a position that is distally beyond the tip.

4. The optical access apparatus according to claim 3, further comprising a control member disposed in mechanical cooperation with the tip and at least partially extending along the obturator sleeve, the control member being actuable to move the tip between the first position and the second position.

5. The optical access apparatus according to claim 1, wherein the tip includes a cutting blade adapted to penetrate tissue.

6. The optical access apparatus according to claim 5, wherein the cutting blade is included on the distal end of the tip.

7. The optical access apparatus according to claim 1, wherein the tip allows light to pass therethrough.

8. The optical access apparatus according to claim 1, wherein distal movement of the tip relative to the obturator sleeve causes the key to disengage the notch thereby permitting rotation of the tip relative to the obturator sleeve.

9. The optical access apparatus according to claim 8, further comprising a control member disposed in mechanical cooperation with the tip and at least partially extending along the obturator sleeve, the control member being actuable to move the tip between the first position and the second position, and the control member being actuable to move the tip distally relative to the obturator sleeve.

10. The optical access apparatus according to claim 9, further comprising a handle disposed in mechanical cooperation with the control member, wherein distal movement of the handle relative to the obturator sleeve actuates the control member and moves the tip distally relative to the obturator sleeve, and wherein rotation of the handle about a handle axis actuates the control member and moves the tip between the first position and the second position.

11. The optical access apparatus according to claim 10, further comprising a bevel gear disposed between the handle and the control member.

12. An optical access apparatus, comprising:
an obturator sleeve defining a passageway, the passageway defining a longitudinal axis and configured to receive surgical instrumentation at least partially therethrough;
a tip disposed adjacent a distal end of the obturator sleeve and configured to separate tissue, the tip being rotatable about an axis of rotation parallel to the longitudinal axis between a first position where a distal end of the tip is in general alignment with the longitudinal axis and a second position where the distal end of the tip is offset from the longitudinal axis, wherein the obturator sleeve includes a notch defined within the distal end thereof, and wherein the tip includes a key configured to selectively engage the notch to help prevent rotation of the tip relative to the obturator sleeve; and
a bevel gear disposed in mechanical cooperation with the tip, wherein rotation of the bevel gear is configured to rotate the tip between the first position and the second position.

13. The optical access apparatus according to claim 12, further comprising a control member disposed in mechanical cooperation with the tip and at least partially extending along the obturator sleeve, the control member being actuable to move the tip between the first position and the second position.

14. The optical access apparatus according to claim 13, wherein the control member is actuable to move the tip distally relative to the obturator sleeve.

15. The optical access apparatus according to claim 13, further comprising a handle disposed in mechanical cooperation with the control member, wherein rotation of the handle about a handle axis actuates the control member and moves the tip between the first position and the second position.

16. The optical access apparatus according to claim 15, wherein the bevel gear is disposed between the handle and the control member.

\* \* \* \* \*